United States Patent [19]

Thielke et al.

[11] Patent Number: 4,837,240
[45] Date of Patent: Jun. 6, 1989

[54] AMINOALKYL SECOCANTHINE DERIVATIVES AND THEIR USE

[75] Inventors: Dietrich Thielke; Dagmar Höltje, both of Gronau, Fed. Rep. of Germany; Guy Nadler, Saint Gregoire, France

[73] Assignee: Beecham-Wuelfing GmbH & Co. KG, France

[21] Appl. No.: 68,625

[22] Filed: Jun. 30, 1987

[30] Foreign Application Priority Data

Jul. 1, 1986 [GB] United Kingdom ................. 8616031
Dec. 22, 1986 [GB] United Kingdom ................. 8630634

[51] Int. Cl.$^4$ .................. A61K 31/395; C07D 471/02
[52] U.S. Cl. ........................................ 514/294; 546/94
[58] Field of Search ........................... 546/94; 514/294

[56] References Cited

U.S. PATENT DOCUMENTS 4,328,343  5/1982  Vollhardt et al. ................... 546/94
4,595,688  1/1986  Maryanoff ............................ 546/94
4,624,954  11/1986  Jirkovsky et al. .................... 546/94

FOREIGN PATENT DOCUMENTS 167901   1/1986  European Pat. Off. ............. 546/94
213696   3/1987  European Pat. Off. ............. 546/94
1550496  8/1979  United Kingdom ................. 546/61
8416724  6/1984  United Kingdom ................. 546/94

OTHER PUBLICATIONS

Yoshio et al., J. Am. Chem. Soc., 1981, 103, 6990-2.
Yoshio et al., Chem. Abstracts, vol. 100, 175109c, (1984).
Yoshio et al., Chem. Abstracts, vol. 96, 20336c, (1982).
Yoshio et al., Chem. Abstracts, vol. 93, 168461v, (1980).
Verpoorte et al., Chem. Abstracts, vol. 100, 64933x, (1984).
Yoshio et al., Chem. Abstracts, vol. 92, 198606t, (1980).
Verpoorte et al., J. Med. Plant Res., 48, (1983), 283-289.

Primary Examiner—Mary C. Lee
Assistant Examiner—Zinna Northington
Attorney, Agent, or Firm—Jacobs & Jacobs

[57] ABSTRACT

A compound of formula (I) or a pharmaceutically acceptable salt thereof:

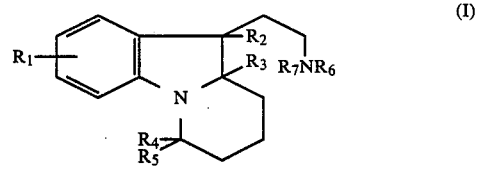

(I)

wherein:

$R_1$ is hydrogen, $C_{1-6}$ alkyl, $C_{1-6}$ alkoxy or halogen;

$R_2$ and $R_3$ are both hydrogen or together represent a bond;

$R_4$ is hydrogen and $R_5$ is hydrogen or $R_4$ and $R_5$ together represent an oxo group;

$R_6$ is phenyl, phenyl $C_{1-7}$ alkyl or phenyl $C_{1-7}$ alkanoyl, in which the phenyl moiety is substituted by $NR_8R_9$ wherein $R_8$ is $C_{1-6}$ alkyl substituted by a group $R_{10}$ selected from hydroxy, halo, $CF_3$ or $COR_{11}$ where $R_{11}$ is hydroxy, $C_{1-4}$ alkoxy or amino optionally substituted by one or two $C_{1-4}$ alkyl groups, and $R_9$ is hydrogen, $C_{1-6}$ alkyl or $R_8$; and $R_7$ is hydrogen or $C_{1-4}$ alkyl.

9 Claims, No Drawings

AMINOALKYL SECOCANTHINE DERIVATIVES AND THEIR USE

This invention relates to compounds having pharmacological activity, to a process for their preparation and their use as pharmaceuticals.

J. Am. Chem. Soc. 1981, 103, 6990–6992 discloses secocanthine derivatives of formula (A):

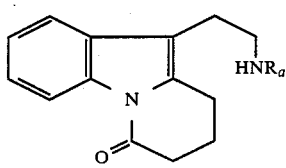

wherein Ra is hydrogen or benzyl. No pharmacological activity is disclosed for these compounds.

EP-0167901-A published 15.01.86 discloses a pharmaceutical composition comprising a compound of formula (B) or a pharmaceutically acceptable salt thereof:

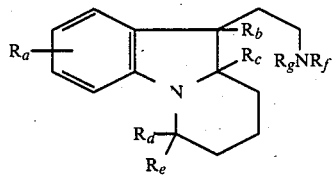

wherein:

$R_a$ is hydrogen, $C_{1-6}$ alkyl, $C_{1-6}$ alkoxy or halogen;

$R_b$ and $R_c$ are both hydrogen or together represent a bond;

$R_d$ is hydrogen and $R_e$ is hydrogen or $R_d$ and $R_e$ together represent an oxo group;

$R_f$ is hydrogen; $C_{1-6}$ alkyl; $C_{3-7}$ cycloalkyl; $C_{3-7}$ cycloalkyl—$C_{1-4}$ alkyl; phenyl or phenyl $C_{1-7}$ alkyl in which the phenyl moiety is optionally substituted by one or two of halogen, ortho-nitro, meta- or para-methoxy, methyl or $NR_hR_i$ wherein $R_h$ and $R_i$ are independently hydrogen or $C_{1-6}$ alkyl or $R_6$ and $R_i$ together are $C_{2-6}$ polymethylene, or 3,4-disubstituted by methylenedioxy or ethylenedioxy; or monocyclic heteroaryl—$C_{-4}$ alkyl or aliphatic heterocyclyl—$C_{1-4}$ alkyl of up to six ring atoms, the heteroatoms(s) being selected from oxygen, sulphur or nitrogen, any amino nitrogen heteroatom optionally $C_{1-4}$ alkyl substituted; and $R_g$ is hydrogen or $C_{1-4}$ alkyl; and a pharmaceutically acceptable carrier.

It is disclosed that the compounds have anti-hypoxic activity and/or activity against cerebral oxygen deficiency and are therefore useful in treating cerebrovascular disorders and disorders associated with cerebral senility.

A further group of secocanthine derivatives have now been discovered to have anti-hypoxic activity and/or activity against cerebral oxygen deficiency, and to improve data acquisition or retrieval following transient forebrain ischaemia.

Accordingly, the present invention provides a compound of formula (I) or a pharmaceutically acceptable salt thereof:

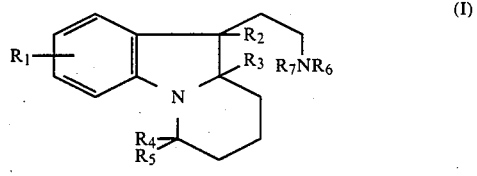

wherein:

$R_1$ is hydrogen, $C_{1-6}$ alkyl, $C_{1-6}$ alkoxy or halogen;

$R_2$ and $R_3$ are both hydrogen or together represent a bond;

$R_4$ is hydrogen and $R_5$ is hydrogen or $R_4$ and $R_5$ together represent an oxo group;

$R_6$ is phenyl, phenyl $C_{1-7}$ alkyl or phenyl $C_{1-7}$ alkanoyl, in which the phenyl moiety is substituted by $NR_8R_9$ wherein $R_8$ is $C_{1-6}$ alkyl substituted by a group $R_{10}$ selected from hydroxy, halo, $CF_3$ or $COR_{11}$ where $R_{11}$ is hydroxy, $C_{1-4}$ alkoxy or amino optionally substituted by one or two $C_{1-4}$ alkyl groups, and $R_9$ is hydrogen, $C_{1-6}$ alkyl or $R_8$; and $R_7$ is hydrogen or $C_{1-4}$ alkyl.

The compounds of the present invention have anti-ischaemic activity, in particular anti-hypoxic activity and/or activity against cerebral oxygen deficiency. The compounds of the invention also improve data acquisition or retrieval following transient forebrain ischaemia. The compounds are therefore useful in the treatment of cerebral vascular and neuronal degenerative disorders associated with learning, memory and cognitive dysfunctions including cerebral senility, multi-infarct dementia and senile dementia of the Alzheimer type.

Suitable examples of $R_1$ include hydrogen, methyl, ethyl, n- and iso-propyl, n-, sec-, iso- and tert-butyl, methoxy, ethoxy, fluoro and chloro. $R_1$ is preferably hydrogen or methyl, most preferably hydrogen.

$R_2$ and $R_3$ preferably together represent a bond.

$R_4$ and $R_5$ are preferably both hydrogen.

Suitable examples of $R_6$ include phenyl, benzyl, benzoyl, phenethyl, 2-methyl-2-phenethyl or 1-methyl-2-phenylethyl in which the phenyl moiety is substituted by hydroxymethylamino, methoxycarbonylmethylamino, 2-hydroxyethylamino, 2-methoxycarbonylethylamino, 2-ethoxycarbonylethylamino, 2-carboxyethylamino, 2-aminocarbonylethylamino or 2,2,2-trifluoroethylamino. Preferably $R_6$ is benzyl, benzoyl, 2-methyl-2-phenethyl or 1-methyl-2-phenylethyl, substituted in the phenyl moiety by $NR_8R_9$ exemplified above.

Suitable examples of $R_7$ include hydrogen, methyl, ethyl, n- and iso-propyl, n-, sec-, iso- and tert-butyl.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

There is a favourable group of compounds within formula (I) of formula (II):

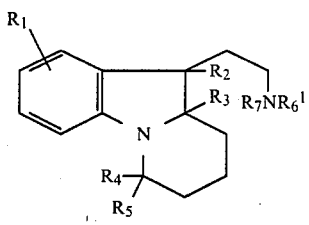

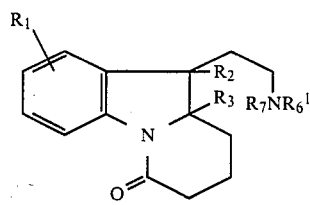

wherein $R_1$, $R_2$, $R_3$, $R_4$, $R_5$ and $R_7$ are as defined in formula (I) and $R_6^1$ is phenyl $C_{1-7}$ alkyl or phenyl $C_{1-7}$ alkanoyl substituted by $NR_8^1R_9^1$ where $R_8^1$ is —$(CH_2)_n$—$R_{10}$ where n is an integer from 1 to 4 and $R_{10}$ is as defined in formula (I), and $R_9^1$ is hydrogen, $C_{1-6}$ alkyl or $R_8^1$.

Suitable and preferred values for $R_1$, $R_2$, $R_3$, $R_4$, $R_5$, $R_6^1$, $R_7$, $R_8^1R_9^1$ and $R_{10}$ are as defined under formula (I) for $R_1$, $R_2$, $R_3$, $R_4$, $R_5$, $R_6$, $R_7$, $R_8$, $R_9$ and $R_{10}$.

n is more preferably 1 to 3, most preferably 2.

There is a sub-group of compounds within formula (II) of formula (IIa):

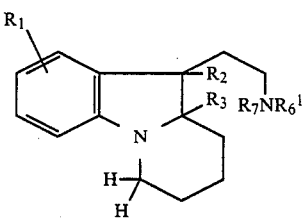

wherein $R_1$, $R_2$, $R_3$, $R_6^1$ and $R_7$ are as defined in formula (II).

Suitable and preferred values for the variables are as described for the corresponding variables under formula (I).

There is a sub-group of compounds within formula (IIa) of formula (IIb):

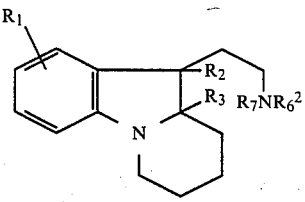

wherein $R_1$, $R_2$, $R_3$ and $R_7$ are as defined in formula (I) and $R_6^2$ is phenyl $C_{1-4}$ alkyl or phenyl $C_{1-4}$ alkanoyl substituted by $NR_8^1R_9^1$ where $R_8^1$ and $R_9^1$ are as defined in formula (II).

Suitable and preferred values for the variables are as described for the corresponding variables under formula (I).

Preferably $R_1$ is hydrogen.

Preferably $R_2$ and $R_3$ represent a bond.

Preferably $R_6^2$ is benzyl, benzoyl, 2-methyl-2-phenethyl or 1-methyl-2-phenylethyl meta- or para-substituted by $NR_8^1R_9^1$.

In $R_6^2$, preferably $NR_8^1R_9^1$ is 2,2,2-trifluoroethylamino, methoxycarbonylmethylamino or 2-hydroxyethylamino.

Preferably $R_7$ is hydrogen.

There is a further group of compounds within formula (II) of formula (III):

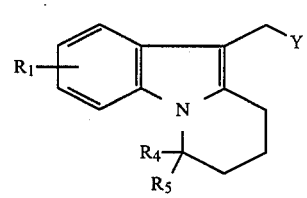

wherein $R_6^1$ is as defined in formula (II) and the remaining variables are as defined in formula (I).

Suitable and preferred values for the variables are as described under formulae (II) and (IIa).

Preferred values for $R_6^1$ are as described for $R_6^2$ under formula (IIb).

Where compounds of formula (I) can exist in more than one stereoisomer form, the invention extends to each of these forms and to mixtures thereof.

The invention further provides a process for the preparation of a compound of formula (I), or a pharmaceutically acceptable salt thereof, which process comprises the conversion of a compound of formula (IV):

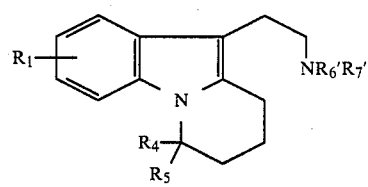

wherein $R_1$, $R_4$ and $R_5$ are as defined in formula (I) and Y is a group convertible to $CH_2NR_6'R_7'$ where $R_6'$ is $R_6$ as defined in formula (I) or a group convertible thereto and $R_7'$ is an amino protecting group or $R_7$ as defined in formula (I), into a compound of formula (V):

(V)

[structure]

and thereafter, optionally and as necessary, converting $R_6'$ when other than $R_6$ into $R_6$ removing any $R_7'$ amino protecting group, interconverting $R_6$ and/or $R_7$ to other $R_6$ or $R_7$, reducing the $R_2/R_3$ bond and/or, when $R_4/R_5$ is oxo, reducing the oxo group to give a compound wherein $R_4$ and $R_5$ are both hydrogen and/or forming a pharmaceutically acceptable salt.

Y may be conventional amine precursor. Suitable examples include CN, COQ where Q is H or a leaving group such as halo, $C_{1-4}$ alkoxy or carboxylic acyloxy, and $CH_2L$ where L is $CON_3$, $N_3$, $NO_2$ or X where X is a leaving group such as hydroxy, halo, $C_{1-4}$ alkoxy, $C_{1-4}$ alkanoyloxy, $C_{1-4}$ alkoxycarbonyloxy, tosyloxy or mesyloxy.

The reaction converting the compound of formula (VI) into that of formula (V) may be carried out under the conventional conditions appropriate to the particular group Y in formula (IV).

Thus, when Y is $CH_2CON_3$, the conversion is a Curtius degradation carried out conventionally, by heating in dry inert solvent, such as benzene, and then subsequent hydrolysis of the thus formed isocyanate under acid conditions.

When Y is CN, the conversion is a reduction to the primary amine, for example with a reducing agent such as diborane or $LiAlH_4$ at elevated temperature and in an inert solvent such as tetrahydrofuran, or with hydrogen over Raney nickel in the presence of ammonia at ambient temperature in a polar solvent such as methanol.

When Y is CHO, the conversion is a condensation with hydroxylamine followed by reduction of the thus formed oxime over a metallic catalyst, or is a reductive amination with a primary or secondary amine using a reducing agent such as $NaBH_3CN$ in a polar solvent such as $CH_2Cl_2/CH_3OH$ at elevated temperature. Alternatively the intermediate imine may be prepared in a non polar solvent such as benzene in the presence of an acid catalyst e.g. p-toluenesulphonic acid and reduced with a reducing agent such as $NaBH_4$.

When Y is COQ where Q is a leaving group, the conversion is a nucleophilic substitution by ammonia or a primary or secondary amine under conventional conditions appropriate for leaving group Q, followed by reduction of the resulting amide with e.g. $LiAlH_4$ in an inert solvent such as tetrahydrofuran at elevated temperature followed by work up. For example, when Q is halo such as chloro, the nucleophilic substitution may be carried out at ambient or lower temperature in the presence of an acid acceptor such as triethylamine in a polar solvent such as $CH_2Cl_2$, followed by work up to give the amide which may be reduced as just described.

When Y is $CH_2N_3$, the conversion is a reduction of the azide to the primary amine with e.g. hydrogen over a metallic catalyst.

When Y is $CH_2NO_2$, the conversion is a reduction of the nitro group to the primary amine with a reducing agent such as $LiAlH_4$, or hydrogen over Raney nickel or Pd/C catalyst in a polar solvent such as ethanol.

When Y is $CH_2X$, the conversion is a nucleophilic substitution by ammonia or a primary or secondary amine or azide ion, under conventional conditions appropriate for the leaving group X. Thus, when X is hydroxy, it is first converted into a good leaving group such as mesylate or tosylate (using mesyl or tosyl chloride respectively) or chloride (using $SOCl_3$). The nucleophilic substitution may be carried out at elevated temperature in a polar solvent such as acetonitrile in the presence of an acid acceptor such as diisopropyl ethylamine. Alternatively, the leaving group may be substituted by nitrile to yield a compound of formula (IV) where $Y=CH_2CN$. Hydrolysis and conversion by conventional methods yields a compound where $Y=CH_2CON_3$ via the acid as described hereinafter.

Suitable examples of $R_6'$ convertible to $R_6$ include hydrogen, an amino protecting group, or phenyl, phenyl $C_{1-7}$ alkyl or phenyl $C_{1-7}$ alkanoyl substituted in the phenyl moiety by a protected amino group or an amine precursor.

In the resulting compound of formula (V) in the case where $R_6'$ or $R_7'$ is an amino protecting group such as $C_{1-6}$ alkoxy carbonyl, aryloxycarbonyl, $C_{1-6}$ alkanoyl or phenyl $C_{1-7}$ alkanoyl, the protecting group may be removed by conventional procedures.

Alternatively, alkanoyl or phenylalkanoyl may be converted directly to alkyl or phenyl alkyl $R_6/R_7$ (as appropriate) by reduction, e.g. with $LiAlH_4$ and $AlCl_3$.

When $R_6'$ is phenyl, phenyl $C_{1-7}$ alkyl or phenyl $C_{1-7}$ alkanoyl substituted with a protected amino moiety, again the protecting group may be removed conventionally or the protected amino group converted to the desired $NR_8R_9$ group by reduction as in the preceding paragraph.

The conversion of any $R_6'$ amino protecting group to an $R_6$ alkyl group via the $R_6'$ hydrogen intermediate, the conversion of $R_6'$ hydrogen to an $R_6$ alkyl group, or the interconversion of an $R_7$ hydrogen atom may be carried out by conventional amine alkylation such as simple alkylation or, more preferably, by acylation followed by reduction of the amide, or by reductive alkylation. The conversion of an $R_6'$ hydrogen atom or an $R_6'$ amino protecting group via hydrogen to an alkanoyl group, may be carried out by conventional amine acylation.

Acylation may be carried out using the appropriate acyl chloride or anhydride and, if necessary, the subsequent reduction of the resulting amide with $LiAlH_4$ in the presence of $AlCl_3$.

The reductive alkylation procedure is preferably carried out by heating with the aldehyde or ketone in an organic acid, such as acetic acid, then reducing the product in situ using an alkaline borohydride such as sodium borohydride or cyanoborohydride. The reaction can also be carried out in an alcohol, in which case the reduction can be carried out either chemically, for example with a borane such as trimethylammoniumborane or an alkaline borohydride or with hydrogen in the presence of a catalyst such as Raney nickel.

It is also possible to use an aprotic solvent, for example an aromatic solvent such as benzene or toluene, the water formed being eliminated either at room temperature by means of a drying-agent or under reflux heating of the solvent by means of a Dean-Stark water-separator; the reduction can then be expediently carried out with hydrogen in the presence of a catalyst such as palladiated carbon or platinum oxide. These methods may be subject to certain limitations, depending on the nature of the aldehyde or ketone used.

It is also possible to use a more universal method. For example, the $R_6'/R_7$ hydrogen compound and the aldehyde or ketone to be condensed are dissolved in a mixture of solvents which can advantageously be a methanol-dichloromethane mixture in the presence of a complex reducing agent such as quaternary ammonium cyanoborohydride or, more simply, an alkaline cyanoborohydride solubilised by a phase-transfer agent, for example sodium cyanoborohydride and aliquat 336 (Cf. Hutchins, R. O. and Markowitz, M., Journal of Organic Chemistry 1981, 46, pp. 3571–3574).

The invention further provides a process for the preparation of a compound of the formula (IIa) or a pharmaceutically acceptable salt thereof in which $R_1$ is hydrogen which process comprises the alkylation or acylation of a compound of the formula (Va):

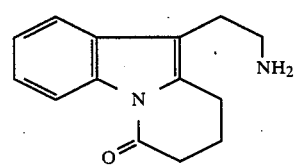

(Va)

followed by, or simultaneously with, the reduction of the $R_4/R_5$ oxo group and, optionally, the reduction of the $R_2/Rhd\ 3$ double bond, and/or the formation of a pharmaceutically acceptable salt.

The alkylation or acylation may be carried out as described above for the conversion of an $R_6'$, or interconversion of an $R_7$, hydrogen atom.

When a phenyl moiety in $R_6'$ is substituted by an amine precursor, conversion of the precursor to amino may be carried out conventionally, as described for the conversions of Y above. Thus, when the precursor is nitro, the conversion may be carried out by catalytic reduction, for example in the presence of Raney nickel.

Substitution of the resulting primary amine by $R_8$ and $R_9$ may be carried out by conventional procedures. Thus conventional amine alkylation, acylation followed by reduction, or reductive alkylation may be employed as described above for the conversion of the $R_6'/R_7$ hydrogen. Interconversion of $R_8$ and $R_9$ may also be carried out conventionally. For example a methoxycarbonylmethyl group may be reduced to hydroxyethyl by treatment with lithium aluminium hydride in tetrahydrofuran.

When $R_6'$ is phenyl $C_{1-7}$ alkanoyl substituted by alkanoylamino, simultaneous reduction of both alkanoyl moieties may be carried out to give the desired compound of formula (I) where $R_6$ is phenyl $C_{1-7}$ alkyl substituted by the corresponding alkyl amino group.

The invention further provides compounds of the formula (Vb):

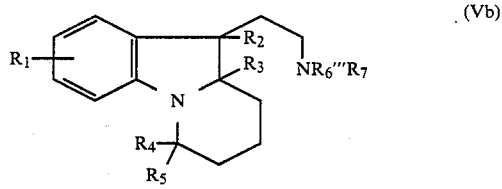

wherein $R_6'''$ is phenyl $C_{1-7}$ alkyl or phenyl $C_{1-7}$ alkanoyl substituted by $NR_8'R_9'$ where $R_8'$ is $C_{1-6}$ alkanoyl substituted by $R_{10}$ as defined in formula (I) and $R_9'$ is $R_9$ as defined in formula (I) or $R_8'$ is $R_8$ as defined in formula (I) and $R_9'$ is $C_{1-6}$ alkanoyl optionally substituted by $R_{10}$, and the remaining variables are as defined in formula (I). Suitable and preferred values for the variables in formula (Vb) are as described for the corresponding variables under formula (I).

When $R_6$ in formula (I) is substituted phenyl, introduction of the phenyl moiety cannot in general be achieved by conversion from $R_6$ hydrogen as discussed above. Instead, the conversion of Y to $CH_2NR_6'R_7'$ will be carried out using aniline as the primary amine, preferably by reductive amination of a Y aldehyde group. However, the presence of an electon withdrawing substituent such as $NO_2$ on the phenyl ring will permit nucleophilic aromatic substitution of the ring by a compound of formula (V) where $R_6'$ is hydrogen with a halogen atom, preferably fluoro, as the leaving group in strong base such as pyridine.

The reduction of the $R_2/R_3$ bond may be carried out conventionally by the use of an alkaline borohydride in a polar aprotic solvent such as dimethylsulphoxide or by nitromethane in the presence of a strong organic acid such as methanesulphonic acid or in pure trifluoroacetic acid. Alternatively the bond may be reduced catalytically with hydrogen over platinum oxide catalyst in a solvent permitting protonation of the indolic nitrogen, such as ethanol containing fluoroboric acid or acetic acid containing trifluoroacetic acid.

When $R_4$ and $R_5$ together form an oxo group, compounds wherein $R_4$ and $R_5$ are both hydrogen may be prepared by reduction of the $R_4/R_5$ oxo group in formula (I) using a mixed hydride complexed with a Lewis acid, for example, the complex aluminium lithium aluminium chloride hydride in an inert solvent such as diethyl ether. When an $R_6$ or $R_7$ alkyl group is introduced initially by acylation to give the amide, simultaneous reduction of the $R_4/R_5$ oxo group and the amide moiety may be effected by appropriate choice of reducing agent, for example the mixed hydride complexed with a Lewis acid just described.

When $R_2$ and $R_3$ together form a bond and $R_4$ and $R_5$ together form an oxo group, simultaneous reduction of the double bond and the oxo group may be effected by the use of an alkaline borohydride as described above for the reduction of an $R_2/R_3$ bond.

It will be appreciated that these conversions may take place in any desired or necessary order.

Pharmaceutically acceptable salts of the compounds of formula (I) may be formed conventionally by reaction with the appropriate acid such as described above under formula (I).

Compounds of formula (IV) in which Y is $CH_2CON_3$ may be prepared by the formation of the acid chloride followed by reaction of azide ion on an acid of formula (VI):

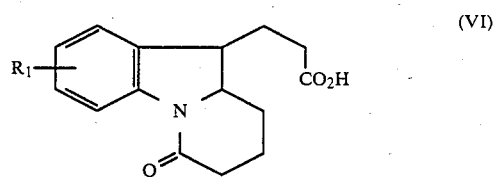

This method is described in J. Am. Chem. Soc. 1981, 103, 6990-6992.

Acids of formula (VI) are known or may be prepared by conventional methods. For example, a phenylhydrazine is condensed with 4-oxoazelaic acid (ref. Von Pechmann et. al. Berichte 1904, 37, p 3816). The hydrazone thus obtained is subjected to a Fischer cyclisation to give the acid of formula (VI).

Compounds of formula (IV) in which $R_4$ and $R_5$ are both hydrogen may be prepared by the reaction of a compound of formula (VII):

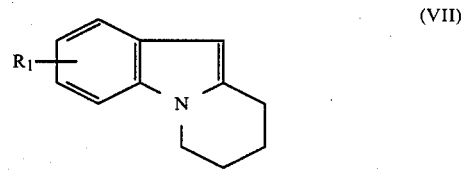

with
(i) $ClCOCOR_{11}$, where $R_{11}$ is alkoxy such as ethoxy or halo such as chloro, followed by reduction with $LiAlH_4$ to give a compound of formula (IV) where Y is $-CH_2OH$ which may subsequently be reacted with azide ion to give the corresponding compound where Y is $-CH_2N_3$;

(ii) $CH_2=CH-R_{12}$, where $R_{12}$ is a 1-carbonyl containing group or cyano, under basic conditions, followed by hydrolysis and reaction on the resulting acid group by azide ion as described above, to give a compound of formula (IV) where Y is $-CH_2CON_3$;

(iii) formaldehyde in the presence of dimethylamine followed by reaction of cyanide ion on the resulting tertiary amine, if necessary after quaternization, to give a compound of formula (IV) where Y is —CN;

(iv) CH$_2$=CHNO$_2$ under basic conditions to give a compound of formula (IV) where Y is CH$_2$NO$_2$.

Compounds of formula (VII) can be prepared according to Hans Zimmer, J. Heterocylic Chemistry 21, 623(1984).

Compounds of formula (IV) in which Y is CHO may be prepared from the corresponding compound in which Y is CN by a variety of conventional procedures such as, for example, reaction with diisobutylaluminium hydride.

Compounds of formula (IV) in which Y is COQ where Q is a leaving group may be prepared from the corresponding compound in which Y is CN by, for example, hydrolysis under acid conditions of the nitrile to give the corresponding acid, followed by conversion of the hydroxyl group to a leaving group Q such as chloro with a chlorinating agent such as oxalyl chloride. Interconversion of leaving groups Q may be carried out conventionally.

Compounds of formula (IV) in which R$_4$ and R$_5$ are both hydrogen and Y is —CH$_2$CN, may alternatively be prepared by homologation of a compound of formula (VIII):

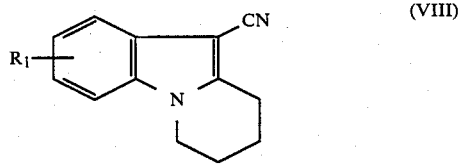

(VIII)

prepared according to D. N. Reinhoudt et al., Tetrahedron Letters 26 (5) 1985, 685-8. The nitrile is first reduced to the amine which is quaternised and reacted with cyanide ion to give the relevant compound of formula (IV).

In the formulae (VI), (VII) and (VIII) above, R$_1$ is as defined in formula (I).

According to the present invention there is also provided a pharmaceutical composition comprising a compound of formula (I), including pharmaceutically acceptable salts thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10-60% by weight, of the active material, depending on the method of administration.

The invention also provides a method of treatment of cerebrovascular disorders and/or disorders associated with cerebral senility in mammals including humans, which comprises administering to the sufferer an effective amount of a compound of formula (I) or a pharmaceutically acceptable salt thereof.

The invention further provides a method of treatment in mammals including humans of cerebral vascular and neuronal degenerative disorders associated with learning, memory and cognitive dysfunctions including cerebral senility, multi-infarct dementia and senile dementia of the Alzheimer type, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 5 to 1000 mg. for example 5 to 500 mg; and such unit doses may be administered more than once a day, for example two or three times a day, so that the total daily dosage is in the range of about 0.1 to 100 mg/kg; and such therapy may extend for a number of weeks or months.

At the above indicated dosage range, no adverse toxicological effects are indicated for the compounds of the invention.

In a further aspect the invention provides a compound of formula (I), including pharmaceutical salts thereof, for use as an active therapeutic substance.

The invention further provides a compound of formula (I), including pharmaceutically acceptable salts thereof, for use in the treatment of cerebrovascular disorders and/or disorders associated with cerebral senility.

In another aspect the invention provides a compound of formula (I), including pharmaceutically acceptable salts thereof, for use in the treatment of cerebral vascular and neuronal degenerative disorders associated with learning, memory and cognitive dysfunctions including cerebral senility, multi-infarct dementia and senile dementia of the Alzheimer type.

The following examples illustrate the invention and the following descriptions illustrate the preparation of intermediates thereto.

DESCRIPTION 1

6-Oxo-6,7,8,9-tetrahydropyrido[1,2-a]indole-10-propionic acid. (D1)

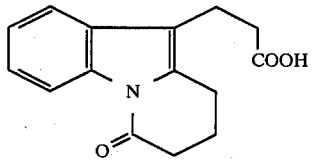

This compound has been described by Y. Ban in J. Amer. Chem. Soc. 1981, 103 (23), pp. 6990–6992. Melting-point 163°–165° C. IR $(KBr)\nu=3200-2500$; 1700; 755 cm$^{-1}$.

DESCRIPTION 2

6-Oxo-10-(2-aminoethyl)-6,7,8,9-tetrahydropyrido[1,2-a]indole hydrochloride (D2)

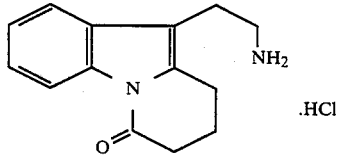

(a) Acid chloride: 1.5 g oxalyl chloride (11.5 mmoles) and 1 drop of DMF were added dropwise to a suspension of 1.5 g (5 mmoles) of the acid of Description 1 in 4 ml benzene. When the liberation of vapours slowed down the mixture was heated for 30 minutes at 60°–70° C. The brown solution thus obtained was concentrated to dryness in vacuo, leaving a residue of maroon-coloured crystals, which were used as they were for stage (b).

(b) Acyl azide: The crude acid chloride from stage (a) was dissolved in 12 ml dry acetone and added dropwise to an ice-cooled solution of 0.4 g sodium azide in 1 ml water and stirred for a further 30 minutes at 0° C., then for 30 minutes at room temperature. The mixture was then diluted with 25 ml water, the precipitate formed was filtered off, washed with water and then dried in vacuo at room temperature, giving the corresponding acyl azide as a white crystalline solid. (c) 56.3 mmoles crude azide from stage (b) was dissolved in 70 ml dry benzene and heated under reflux for 40 minutes. There was a substantial liberation of nitrogen and the solution turned black. 100 ml benzene and 24 ml concentrated HCl were then added and heated under reflux for 1 hour. There was a substantial liberation of gas/vapours, and then a precipitate was formed. The solution was then concentrated to dryness, giving the crude amine hydrochloride. Recrystallisation in a 4/1 mixture of ethanol/water produced a white crystalline solid D2 described by Y. Ban (ref.cited) of m.pt. 330°–335° C. (decomposition). IR $(KBr)\nu=3200-2400$; 1700; 745 cm$^{-1}$. UV (ethanol)$\lambda$max=243; 267; 292; 302 nm.

DESCRIPTION 3

6-Oxo-10-[2-(3-nitrobenzoyl)aminoethyl]-6,7,8,9-tetrahydropyrido[1,2-a]indole (D3)

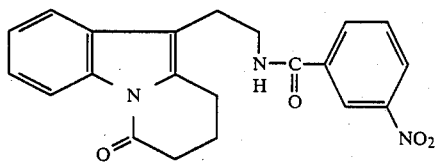

A solution of 19 g m-nitrobenzoyl chloride in 50 ml CHCl$_3$ (chloroform) was added dropwise to an ice-cooled suspension of 24 g compound D2 and 25 g triethylamine in 300 ml CHCl$_3$. After total solubilisation a precipitate was formed. The mixture was left to stand for 4 hours at room temperature, then filtered. The crystals were washed with CH$_2$Cl$_2$, water and ether. 25.2 g of D3 was obtained.
m.pt 215° C.
IR(KBr)$\nu=3260$; 3100–2800; 1690; 750; 720; 680; 650 cm$^{-1}$

DESCRIPTION 4

6-Oxo-10-[2-(3-aminobenzoyl)aminoethyl]-6,7,8,9-tetrahydropyrido[1,2-a]indole hydrochloride (D4)

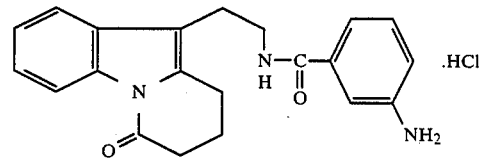

Compound D3 (29 g) was hydrogenated at room temperature at a pressure of 10 bar for 12 hours in 500 ml DMF in the presence of 5 g of Raney nickel. The catalyst was filtered of, the DMF concentrated and the amine acidified with ethanol/hydrochloric acid, giving 16 g of D4.
m.pt 240° C.
IR(KBr)$\nu=3340$; 3000–2500; 1660; 760 cm$^{-1}$
M.S. empirical formula C$_{21}$H$_{21}$N$_3$O$_2$
M.W. found: 347.1635; theory 347.163366 m/e (% relative intensity) 347(M$^+$,20); 211(100); 198(11); 172(27).

DESCRIPTION 5

6-Oxo-10-[2-(3-(2,2,2-Trifluoroacetyl)aminobenzoyl)aminoethyl]-6,7,8,9-tetrahydropyrido[1,2-a]indole (D5)

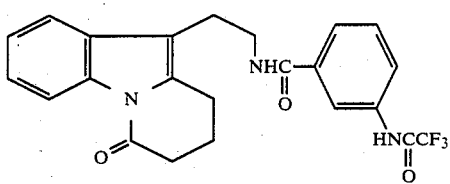

8 g Compound D4 was treated at room temperature with 9 ml trifluoroacetic anhydride. After working up, 4.7 g acetamide D5 was obtained.

DESCRIPTION 6

10-(2-Aminoethyl)-6,7,8,9-tetrahydropyrido[1,2-a]indole hydrochloride. (D6)

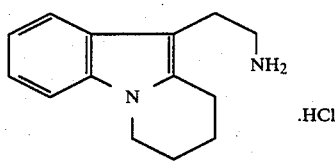

15 g Compound D2 was added in small fractions to a suspension of 17 g AlCl$_3$ and 7 g LiAlH$_4$ in 150 ml dry ether and 150 ml dry tetrahydrofuran. It was left for 1 hour at room temperature, then the excess hydride was destroyed with water and sodium hydroxide. It was filtered on Clarsel, concentrated, taken up in CH$_2$Cl$_2$, the solution washed with water, dried and acidified with ethanol/HCl, giving 10 g white crystals of D6. m.pt.=288°–290° C. IR(KBr)$\nu$=3300–2400; 740 cm$^{-1}$ UV(CH$_3$OH)$\lambda$max=240; 285; 26 nm M.S. empirical formula: C$_{14}$H$_{18}$N$_2$ M.W. found: 214.1469; theory: 214.1469 m/e (% relative intensity) 214(M$^+$, 18); 184(100); 156(11)

DESCRIPTION 7

10-(2-(4-Nitrobenzoyl)-aminoethyl)-6,7,8,9-tetrahydropyrido (1,2-a) indole (D7)

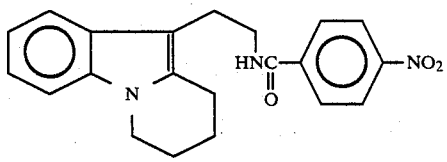

A solution of 10 g p-nitrobenzoyl chloride in 50 ml of chloroform was added dropwise to a suspension of the amine hydrochloride (D6) and 25 ml triethylamine in 300 ml chloroform. The mixture was left to stand for 2 hours at room temperature, then shaken with citric acid solution, sodium carbonate solution and brine, dried and evaporated. Crystallisation from diisopropyl ether yielded 13.2 g, m.pt: 184°–5° C.

DESCRIPTION 8

10-(2-(4-Aminobenzoyl)-aminoethyl)-6,7,8,9-tetrahydropyrido-(1,2-a)-indole hydrochloride (D8)

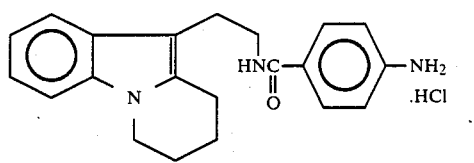

Compound D7 was hydrogenated at room temperature at a pressure of 4 bar for 24 hours in trifluoroacetic acid in the presence of 1 g Pd/C. The catalyst was filtered off, the solution concentrated, taken up in methylene chloride, shaken with sodium carbonate solution, dried, evaporated and the amine acidified with ethanol/HCl giving 9.6 g D8. m.pt: 210° C. dec. Nmr (DMSO d6) $\delta$=1.7–2.3[4] m, 4 [2] tr J=6 Hz 6.9–8 [8] m

EXAMPLE 1

10-[2-(3-(2,2,2-Trifluoroethyl)aminobenzyl)aminoethyl]-6,7,8,9-tetrahydropyrido[1,2-a]indole dihydrochloride (E1)

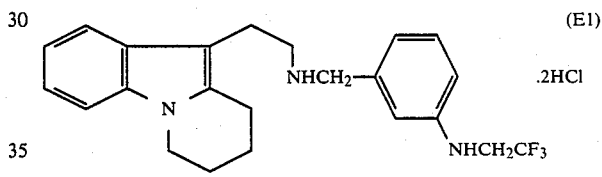

The acetamide D5 was reduced with a mixture of LiAlH$_4$ (2.4 g), AlCl$_3$ (5.4 g) and ether (200 ml). After working up and acidification with EtOH/HCl the hydrochloride was crystallised from CH$_3$CO$_2$C$_2$H$_5$ giving 0.7 g crystals of E1.

m.pt=205° C.
IR(KBr)$\nu$=3300; 3000–2500; 1610; 1160; 1140; 740 cm$^{-1}$
UV(CH$_3$OH) $\lambda$max=230; 245; 288; 294 nm
M.S. empirical formula: C$_{23}$H$_{26}$N$_3$F$_3$
M.W. found: 401.2086; theory 401.207668
m/e(% relative intensity)
401(M+2.5); 217(3.8); 188(22); 185(100); 184(81); 183(15); 156(9)

EXAMPLE 2

10-(2-(4-(Methoxycarbonylmethylamino)benzoyl)amino-ethyl)-6,7,8,9-tetrahdryopyrido[1,2-a]indole hydrochloride (E2)

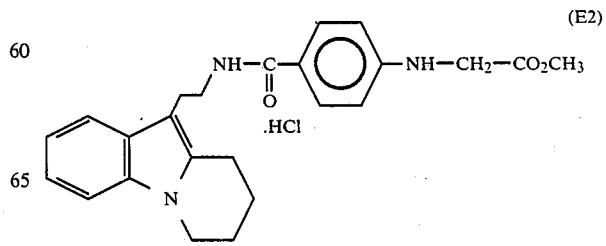

8.5 g of D8 were dissolved in 100 ml of methanol and 25 ml of di-isopropylethylamine and 6 ml of methyl bromoacetate added. The solution was refluxed for 120 h and evaporated. The residue was taken up in methylenechloride, and shaken with citric acid solution and sodium carbonate solution. The organic layer was dried, evaporated and the product crystallised from ethylacetate/diisopropylether and converted to the hydrochloride.

m.p.: 179° C. (dec.)
NMR (base): CDCl₃
δ: 7.50[3]m; 7.15[3]m; 6.50[2]m; 6.07[1]m; broad; 4.57[1]m; broad; 4.20–3.50[9]m; 2.95[4]m; 1.95[4]m.

EXAMPLE 3

10-(2-(4-(2-Hydroxyethyl)-aminobenzyl)-aminoethyl)-6,7,8,9-tetrahydropyrido[1,2-a]indole dihydrochloride (E3)

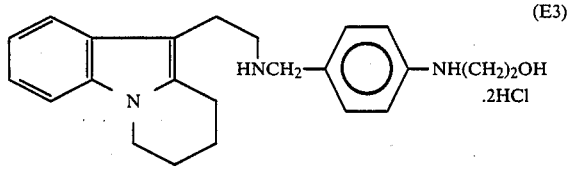

The residue from Example 2 was dissolved in 100 ml of tetrahydrofuran and added to a suspension of 2 g of lithium aluminium hydride in the same solvent and heated to reflux for 2 h. The excess hydride was destroyed with water and sodium hydroxide. It was filtered, concentrated, taken up in methylene chloride, the solution washed with water, dried and acidified with ethanol/HCL giving 2 g of product. Recrystallisation from ethanol/ethyl acetate yielded 1 g of the dihydrochloride m.pt: 203°–5° C.

EXAMPLE 4

10-(2-(3-(Methoxycarbonylmethylamino)benzoyl-)amino-ethyl)-6-oxo-6,7,8,9-tetrahydropyrido[1,2-a]indole hydrochloride (E4)

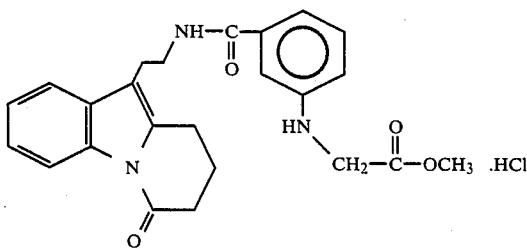

21 g D 4 were dissolved in 200 ml acetonitrile and 60 ml diisopropylethylamine, and 10 ml methyl bromacetate was added. The solution was heated for 20 h at 60° C. and evaporated.

The residue was taken up in methylenechloride, shaken with citric acid solution, sodium carbonate solution and brine, dried and evaporated.

The product was purified by column chromatography and ethanol/hydrochloric acid was added to yield the hydrochloride.

Yield 13 g
M.pt. 690° C.
NMR (CDCl₃) δ=8.45[1]m; 6.6–7.7 [8] m 1 exchange; 6.28 [1] tr broad exchange; 3.4–4[8] m; 2.6–3.1 [6] m; 2.03 [2] m.

EXAMPLE 5

10-(2-(3-(2-Hydroxyethyl)-aminobenzyl)-aminoethyl)-6,7,8,9-tetrahydropyrido[1,2-a]indole dihydrochloride (E5)

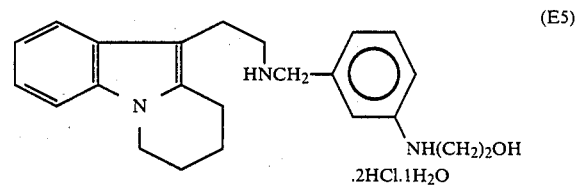

10.5 g of E4 (as base) were dissolved in 200 ml tetrahydrofuran and added to a suspension of 6 g lithium aluminium hydride and 12 g AlCl₃ in the same solvent and stirred at room temperature for 8 h. The excess hydride was destroyed with water and sodium hydroxide.

It was filtered, concentrated, taken up in methylene chloride, the solution washed with water, dried and acidified with ethanol/HCl giving 2.6 g of product.

Recrystallisation from ethanol/ethyl acetate yielded 2 g dihydrochloride.

M.pt.: 162° C.
NMR (DMSO d₆)δ=6.8–7.7 [8] m; 3.8–4.3 [4] m (after exchange 4.2 [2] s and 4 [2] tr J=6 Hz); 1.7–7.2 [4] m

PHARMACOLOGICAL DATA

1. Triethyltin-induced cerebral oedema in the rat

The cerebral oedema is induced by oral administrations repeated for 5 consecutive days—one administration per day—of triethyltin chloride at a dose of 2 mg/kg. The study substances are also administered orally twice daily as aqueous solution or suspension at a dose of 1 ml/100 g body-weight; these administrations are given during the 5 days of intoxication with tin. Three groups of 10 male specific pathogen-free (SPF) Wistar rats of 280±10 g body-weight are used for each compound studied:

1 control group
1 group intoxicated with triethyltin
1 group intoxicated with triethyltin and treated with the studied compound.

The rats are sacrificed on the evening of the fifth day; the brain is removed, weighed fresh and after desiccation to constant weight and the water content of each brain is calculated: [H₂O]=fresh weight—dry weight.

The following are then calculated:
the mean water content (M±Sm%) of each group;
the protection index P due to the administered compound:

$$P\% = 1 - \frac{[H_2O] \text{ treated group} - [H_2O] \text{ control group}}{[H_2O] \text{ triethyltin group} - [H_2O] \text{ control group}} \times 100$$

The results are shown in Table 1:

TABLE 1

| Compound | Dose mg/kg p.o. | P % | Significance* |
|---|---|---|---|
| E3 | 2 × 12.5 | 47 | p < 0.01 |
| E5 | 2 × 12.5 | 41 | p < 0.01 |

*unpaired Wilcoxon signed rank test.

2. The Gerbil Ischaemic Deficit Passive Avoidance Test

Mongolian gerbils were conditioned to avoid entering a dark compartment by means of a footshock (maximally 50 V, 2 s duration) received when entering from the light section of a two compartment box. Recollection of the footshock was examined 24 h later by replacing the gerbils in the two compartment box and measuring the recall latency, the time taken to re-enter the dark compartment.

Effect of test compound on recall latency in the gerbil following transient forebrain ischaemia (a) Animal Preparation A learning or memory deficit was induced in the gerbils by a transient (5 min) bilateral carotid artery ligation, performed 24 h prior to conditioning, under light hexobarbital anaesthesia.

(b) Measurement

Compounds, being examined for an effect on learning or memory in gerbils which had undergone carotid occlusion, were administered seven times during the experiment. The initial administration was during the period of forebrain ischaemia, the third and seventh administrations were 10 min prior to conditioning and recall testing, respectively, and the remainder were given at intermediate time points.

Results were expressed as percentage of animals which had a long recall latency (>60 s). A long recall latency indicates good information acquisition or retrival.

(c) Results

The results for compound E5 are shown in Table 2.

TABLE 2

| | | Percentage of animals with recall latencies >60s |
|---|---|---|
| I | sham-ligated controls | 33** |
| II | Ischaemic controls | 14 |
| III | Ischaemia and Compound E5 (3 mg/kg) | 39* | significantly different from II (*p<0.05, **p<0.01)

As can be seen in Table 2, transient cerebral ischaemia impairs the recollection of the footshock in gerbils. Compound A significantly increased the percentage of animals with long recall latencies.

The above results show that compound E5 improves data acquisition or retrieval in the gerbil following transient forebrain ischaemia and demonstrate that the compounds of the invention are of potential use in the treatment of cerebral vascular and neuronal degenerative disorders associated with learning, memory and cognitive dysfunctions including cerebral senility, multi-infarct dementia and senile dementia of the Alzheimer type.

What is claimed is:

1. A compound of formula (I) or a pharmaceutically acceptable salt thereof:

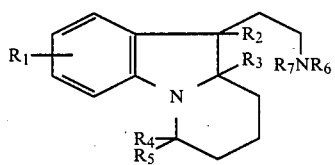

wherein:
$R_1$ is hydrogen, $C_{1-6}$ alkyl, $C_{1-6}$ alkoxy or halogen;
$R_2$ and $R_3$ are both hydrogen or together represent a bond;
$R_4$ is hydrogen and $R_5$ is hydrogen or $R_4$ and $R_5$ together represent an oxo group;
$R_6$ is phenyl, phenyl $C_{1-7}$ alkyl or phenyl $C_{1-7}$ alkanoyl, in which the phenyl moiety is substituted by $NR_8R_9$ wherein $R_8$ is $C_{1-6}$ alkyl substituted by a group $R_{10}$ selected from hydroxy, halo, $CF_3$ or $COR_{11}$ where $R_{11}$ is hydroxy, $C_{1-4}$ alkoxy or amino optionally substituted by one or two $C_{1-4}$ alkyl groups, and $R_9$ is hydrogen, $C_{1-6}$ alkyl or $R_8$; and
$R_7$ is hydrogen or $C_{1-4}$ alkyl.

2. A compound according to claim 1, wherein $R_1$ represents hydrogen, $R_2$ and $R_3$ represent a bond and $R_7$ represents hydrogen.

3. A compound according to claim 1, wherein $R_4$ and $R_5$ each represent hydrogen.

4. A compound according to claim 1, wherein $R_6$ represents phenyl $C_{1-4}$ alkyl or phenyl $C_{1-4}$ alkanoyl substituted by $NR_8{}^1R_9{}^1$ were $R_8{}^1$ is $-(CH_2)_n{}'R_{10}$ where n is an integer from 1 to 4 and $R_{10}$ is as defined in claim 1 and $R_9{}^1$ is hydrogen, $C_{1-6}$ alkyl or $R_8{}^1$.

5. A compound according to claim 1, wherein $NR_8R_9$ represents 2,2,2-trifluoroethylamino, methoxycarbonylmethylamino or 2-hydroxyethylamino.

6. 10-[2-(3-(2,2,2-Trifluoroethyl)aminobenzyl)aminoethyl]-6,7,8,9-tetrahydropyrido[1,2-a]indole,
  10-(2-(4-(methoxycarbonylmethylamino)benzoyl)amino-ethyl)-6,7,8,9-tetrahydropyrido[1,2-a]indole,
  10-(2-(4-(2-hydroxyethyl)-aminobenzyl)-aminoethyl)-6,7,8,9-tetrahydropyrido[1,2-a]indole,
  10-(2-(3-(methoxycarbonylmethylamino)benzoyl)amino-ethyl)-6-oxo-6,7,8,9-tetrahydropyrido[1,2-a]indole or
  10-(2-(3-(2-hydroxyethyl)-aminobenzyl)-aminoethyl)-6,7,8,9-tetrahydropyrido[1,2-a]indole, or a pharmaceutically acceptable salt thereof.

7. A pharmaceutical composition for use in the treatment of cerebral vascular and neuronal degenerative disorders associated with learning, memory and cognitive dysfunctions including cerebral senility, multi-infarct dementia and senile dementia of the Alzheimer type, which comprises an effective amount of a compound according to claim 1 in combination with a pharmaceutically acceptable carrier.

8. A method of treatment in mammals including humans of cerebral vascular and neuronal degenerative disorders associated with learning, memory and cognitive dysfunctions including cerebral senility, multi-infarct dementia and senile dementia of the Alzheimer type, which comprises administering to the sufferer an effective amount of a compound according to claim 1.

9. A pharmaceutical composition comprising a compound according to claim 1 and a pharmaceutically acceptable carrier.

* * * * *

UNITED STATES PATENT AND TRADEMARK OFFICE
CERTIFICATE OF CORRECTION

PATENT NO.  : 4,837,240
DATED       : June 6, 1989
INVENTOR(S) : Dietrich Thielke, et al It is certified that error appears in the above-identified patent and that said Letters Patent is hereby corrected as shown below: On the title page:

Please change identification of the Assignee to read as follows:

--Beecham-Wuelfing GmbH & Co. KG,
  West Germany
  Laboratories Sobio SA
  France--

Signed and Sealed this

Eighth Day of May, 1990

Attest:

HARRY F. MANBECK, JR.

Attesting Officer

Commissioner of Patents and Trademarks